United States Patent [19]
Sarvazyan

[11] Patent Number: 5,833,633
[45] Date of Patent: *Nov. 10, 1998

[54] DEVICE FOR BREAST HAPTIC EXAMINATION

[75] Inventor: Armen Paruir Sarvazyan, East Brunswick, N.J.

[73] Assignee: Artann Laboratories, Lambertville, N.J.

[*] Notice: The term of this patent shall not extend beyond the expiration date of Pat. No. 5,524,636.

[21] Appl. No.: 963,385

[22] Filed: Nov. 3, 1997

Related U.S. Application Data

[60] Division of Ser. No. 607,646, Feb. 27, 1996, which is a continuation-in-part of Ser. No. 994,109, Dec. 21, 1992, Pat. No. 5,524,636.

[51] Int. Cl.$^6$ ...................................................... A61B 8/12
[52] U.S. Cl. ........................ 600/587; 600/561; 600/437; 73/787; 73/818
[58] Field of Search ...................................... 600/587, 561, 600/437; 73/818, 788, 789, 790, 794–6, 798

[56] References Cited

U.S. PATENT DOCUMENTS

| | | | |
|---|---|---|---|
| 4,250,894 | 2/1981 | Frei et al. | 600/587 |
| 4,947,851 | 8/1990 | Sarvazyan | 600/437 |
| 5,278,776 | 1/1994 | Fisher et al. | 600/587 |
| 5,293,870 | 3/1994 | Ophir et al. | 600/437 |
| 5,524,636 | 6/1996 | Sarvazyan et al. | 600/587 |

*Primary Examiner*—Robert L. Nasser
*Attorney, Agent, or Firm*—Mathews, Collins, Shepherd & Gould, P.A.

[57] ABSTRACT

In one embodiment of the invention, a pressure sensor array, data acquisition circuit, and a microprocessor are mounted in a hand held pad. Detection of nodules is achieved by analyzing the dynamic and spatial features of the pressure pattern while the probe pressed to the breast is periodically moved transversely to the ribs. The ribs play a role as an amplifier of the measured effect. The device will be able to objectively detect the presence of lumps in a breast and provide a warning signal. Another embodiment of the invention is a clinical device for imaging the mechanical structure of the examined breast and diagnosing diseases accompanied by changes in the elasticity of breast tissue. This embodiment is made up of an electronically controlled mechanical scanning unit incorporated into a patient support bed. The mechanical scanning unit includes a compression mechanism and positioning system, a local pressure source located opposite a pressure sensor array, and electronic control and interface circuitry. The local pressure source is either a roller moving over the examined breast, or in another embodiment, an indenter which can be moved in all three dimensions and be controlled either automatically by a computer or manually by a mouse. In yet another embodiment, the mechanical scanning system serves as a biopsy guidance means and determines target lesions in the breast to be reached by a biopsy gun or aspiration needle.

10 Claims, 10 Drawing Sheets

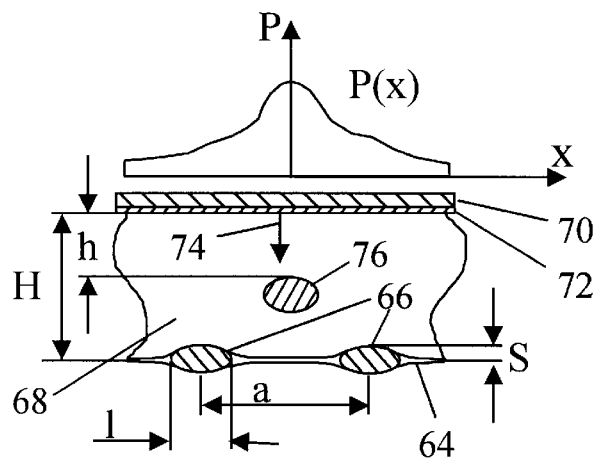
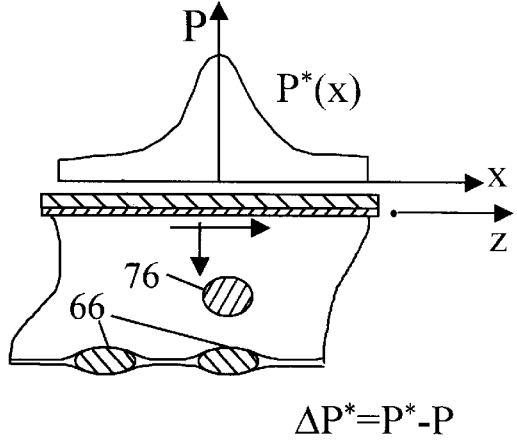
Fig. 1A  Fig. 1B
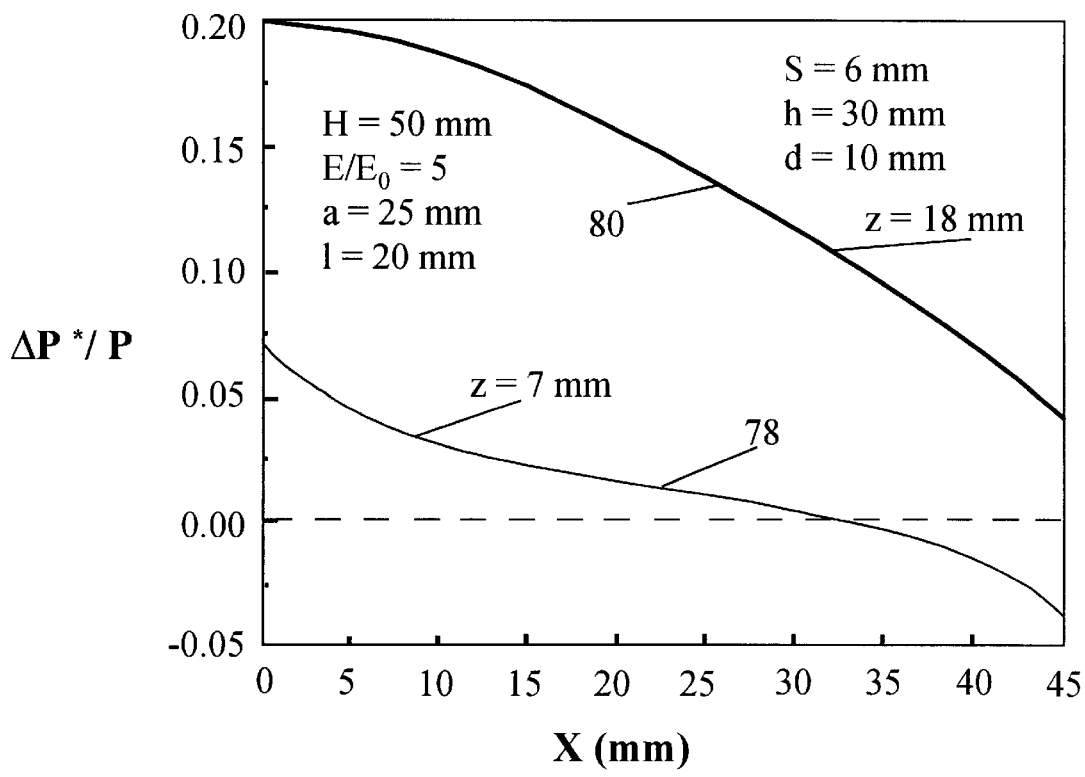
Fig. 1C

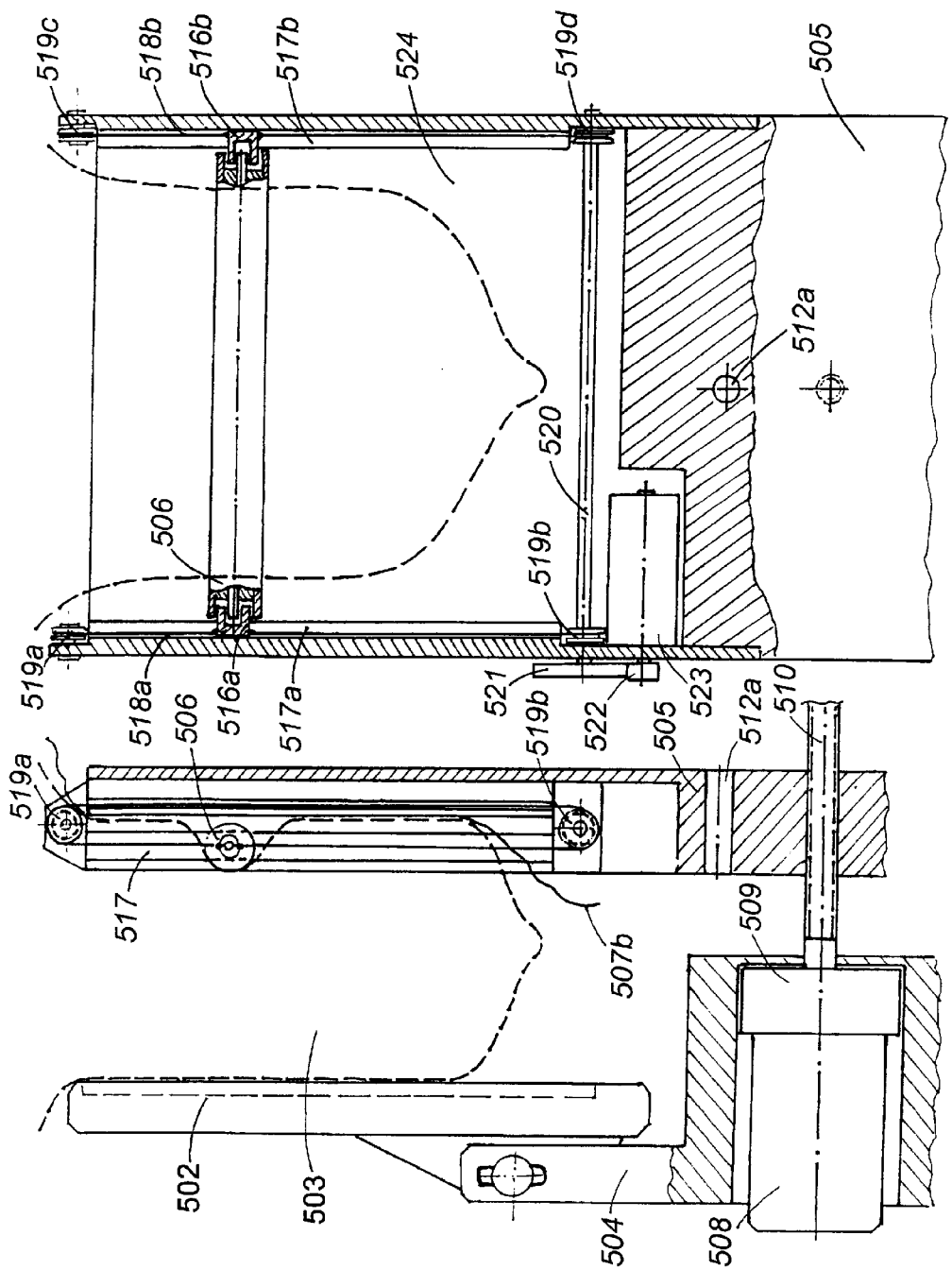

Fig. 11A
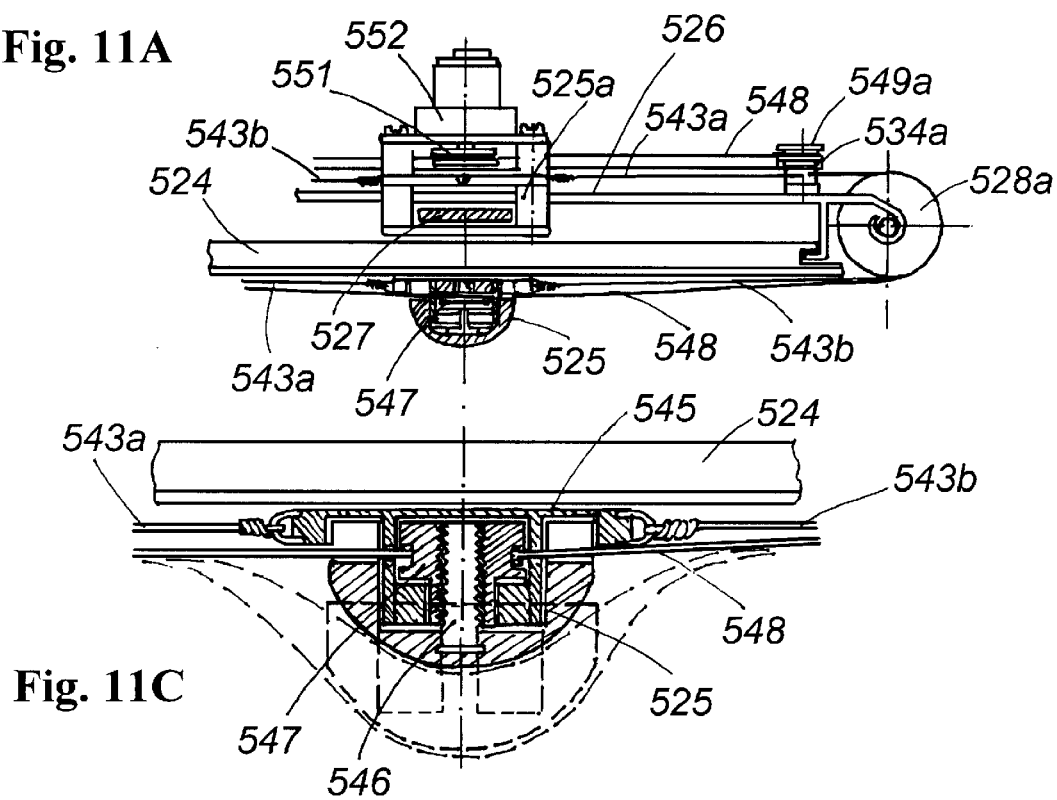
Fig. 11C
Fig. 11B
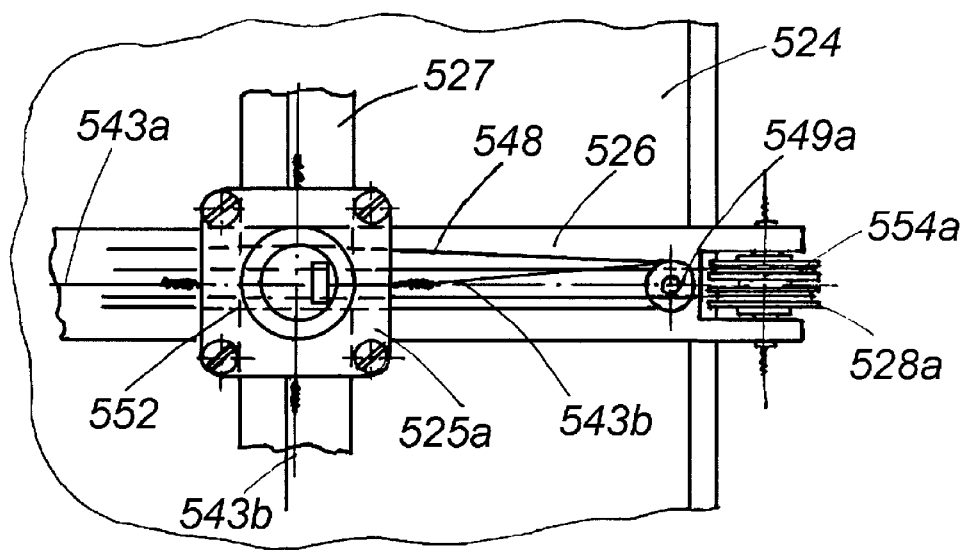

DEVICE FOR BREAST HAPTIC EXAMINATION

CROSS REFERENCE TO RELATED APPLICATION

This application is a division of application Ser. No. 08/607,646 filed Feb. 27, 1996 which application is now: pending, which application is a continuation-in-part of Ser. No. 07/994,109, filed Dec. 21, 1992, now. U.S. Pat. No. 5,524,636.

This invention was made with government support under SBIR Grant No.1 R43 CA65246-01 A1 awarded by the National Institute of Health, National Cancer Institute. The government has certain rights in this invention.

BACKGROUND OF THE INVENTION

1. Technical Field

The present invention relates to a method and apparatus for detecting regions in the tissue with the elasticity different from that of the surrounding tissues using a pressure sensing array for diagnosing breast cancer and other breast diseases accompanied by changes in the tissue elasticity.

2. Description of the Prior Art

Diagnosing early formation of tumors, particularly those caused by cancer, has been a problem that has been attempted to be solved using various techniques, such as ultrasonic imaging, nuclear magnetic resonance imaging, x-rays, and the like. Each of these techniques have limitations, including the application of radiation to the body, which may be harmful to the body being tested.

One of the safest and oldest techniques of detecting diseased tissue is palpation. Palpation, that is, examination using the sense of touch, is based on the significant differences in elasticity of normal tissues and certain lesions. Palpation has been a commonly used technique for detecting prostate and breast cancer. Surprisingly, over 90% of breast cancer is first detected by women themselves (Strax P., *Control of breast cancer through mass screening*, Hospimedica, March/April, pp. 35—40 (1989)), in spite of palpation being very subjective, not able to detect tumors of less than about 8 mm in diameter, and, besides, being capable of sensing lumps only when their elastic modulus is a few times higher than that for normal glandular tissue. Nevertheless, the manual palpation till now is one of the major methods of clinical examination of the breast just because of the great scale changes of mechanical properties of tissues in the course of development of cancer. Many tumors that are currently considered "nonpalpable" because of their small size or insufficiently high Young's modulus, nevertheless, can be detected mechanically if a more sensitive instrument than a finger could be used. Thus, development of a method that will enable physicians to obtain quantitative objective information on changes of elasticity of breast tissues with sensitivity and spatial resolution considerably higher than that of palpation would be a significant step in the early diagnostics of breast cancer.

Various types of devices mimicking palpation to detect tumors using different types of pressure sensors have been suggested. For example, Frei et al., U.S. Pat. No 4,250,894, have proposed an instrument for breast examination that uses a plurality of spaced piezoelectric strips which are pressed into the body being examined by a pressure member which applies a given periodic or steady stress to the tissue beneath the strips. A different principle for evaluating the pattern of pressure distribution over a compressed breast was proposed by Gentle (Gentle CR, *Mammobarography: a possible method of mass breast screening*, J. Biomed. Eng. 10, 124–126, 1988). The pressure distribution is monitored optically by using the principle of frustrated total internal reflection to generate a brightness distribution. Using this technique, referred to as "mammobarography," simulated lumps in breast prostheses have been detected down to a diameter of 6 mm. According to Gentle, this technique can be used for mass breast screening; however, no quantitative data on lumps in a real breast was ever published. The failure has been explained by the insufficient sensitivity of the registration system. It should be noted, that most of the development of pressure sensors for medical applications has been done not for mimicking palpation but for monitoring blood pressure and analyzing propagation of pulse waves in blood vessels (See, for example, U.S. Pat. Nos. 4,423,738; 4,799,491; 4,802,488; 4,860,761).

Another approach to evaluate elasticity of the tissues uses indirect means, such as conventional imaging modalities (ultrasound or MRI) which are capable to detect motion of a tissue subjected to an external force. One approach attempts to determine the relative stiffness or elasticity of tissue by applying ultrasound imaging techniques while vibrating the tissue at low frequencies. See. e.g., K. J. Parker el al, U.S. Pat. No. 5,099,848; R. M. Lerner el al., *Sono-Elasticity: Medical Elasticity Images Derived From Ultrasound Signals in Mechanically Vibrated Targets*, Acoustical Imaging, Vol. 16, 317 (1988); T. A. Krouskop et al.,*A Pulsed Doppler Ultrasonic System for Making Non-Invasive Measurement of Mechanical Properties of Soft Tissue*, 24 J. Rehab. Res. Dev. Vol. 24, 1 (1987); Y. Yamakoshi et al., *Ultrasonic Imaging of Internal Vibration of Soft Tissue Under Forced Vibrations*, IEEE Transactions on Ultrasonics, Ferroelectrics, and Frequency Control, Vol. 7, No. 2, Page 45 (1990).

Another method proposed for measuring and imaging tissue elasticity is described in Ophir et al., U.S. Pat. Nos. 5,107,837, 5,293,870, 5,143,070 and 5,178,147. This method includes emitting ultrasonic waves along a path into the tissue and detecting an echo sequence resulting from the ultrasonic wave pulse. The tissue is then compressed (or alternatively decompressed from a compressed state) along the path and during such compression, a second pulse of ultrasonic waves are sent along the path into the tissue. The second echo sequence resulting from the second ultrasonic wave pulse is detected and then the differential displacement of selected echo segments of the first and second echo sequences are measured. A selected echo segment of the echo sequence, i.e., reflected RF signal, corresponds to a particular echo source within the tissue along the beam axis of the transducer. Time shifts in the echo segment are examined to measure compressibilities of the tissue regions.

Thus, since current prior art methods and devices for detecting lesions in breast by evaluating tissue elasticity are inferior to manual palpation, there still remains a need for a simple and effective device for the detection of breast cancer.

SUMMARY OF THE INVENTION

The method and devices in accordance with the present invention enable the user to detect regions of breast tissue having elasticity modulus different from that of surrounding glandular tissue using a pressure sensing array. Detection of breast tumors is based on analyzing features of the stress pattern on the surface of an examined tissue that appear as a deviation from a stress pattern for a relatively homogeneous normal tissue.

In one embodiment of the invention a pressure sensor array, data acquisition circuit, and a microprocessor are mounted in a hand held pad. Detection of nodules is achieved by analyzing the dynamic and spatial features of the pressure pattern while the probe pressed to the breast is periodically moved transversely to the ribs. The ribs play a role as amplifier of the measured effect. The device will be able to objectively detect the presence of small lumps in a breast (e.g., about 5 mm in diameter) and provide a warning signal.

Another embodiment of the invention is a clinical device for imaging mechanical structure of the examined breast and diagnosing diseases accompanied by changes in the elasticity of breast tissue. This embodiment comprises electronically controlled mechanical scanning unit incorporated into a patient support bed. The mechanical scanning unit includes a compression mechanism and positioning system, a local pressure source opposing a pressure sensor array, and electronic control and interface circuitry. The local pressure source is an indenter which can be moved in all three dimensions.

In another embodiment, the mechanical scanning system serves as a biopsy guidance means and determines target lesions in the breast to be reached by the biopsy gun or aspiration needle.

BRIEF DESCRIPTION OF THE DRAWINGS

FIG. 1A is a graphical representation of tissue positioned over underlying objects such as ribs, and being loaded in accordance with the present invention;

FIG. 1B is an illustration similar to that shown in FIG. 1A with the outer surface of the tissue shifted relative to the supporting ribs;

FIG. 1C is a graphical representation of the changes in pressure profile after a shift of the outer surface of the tissue has been made, as shown in FIG. 1B;

FIG. 2A ia a graphical representation of the moved stress curve on a X-axis direction with a hardened area or tumor being moved by the roller of FIG. 2;

FIG. 9A is a detailed sectional side view of the roller motion control system of the mechanical scanning unit shown in FIG. 8;

FIG. 9B is a detailed front view of the roller motion control system of the mechanical scanning unit shown in FIG. 8;

FIGS. 11A–C are enlarged fragmentary views of the indenter and its motion controlling cables shown in FIGS. 10A and B.

DETAILED DESCRIPTION OF THE INVENTION

Figure 2:
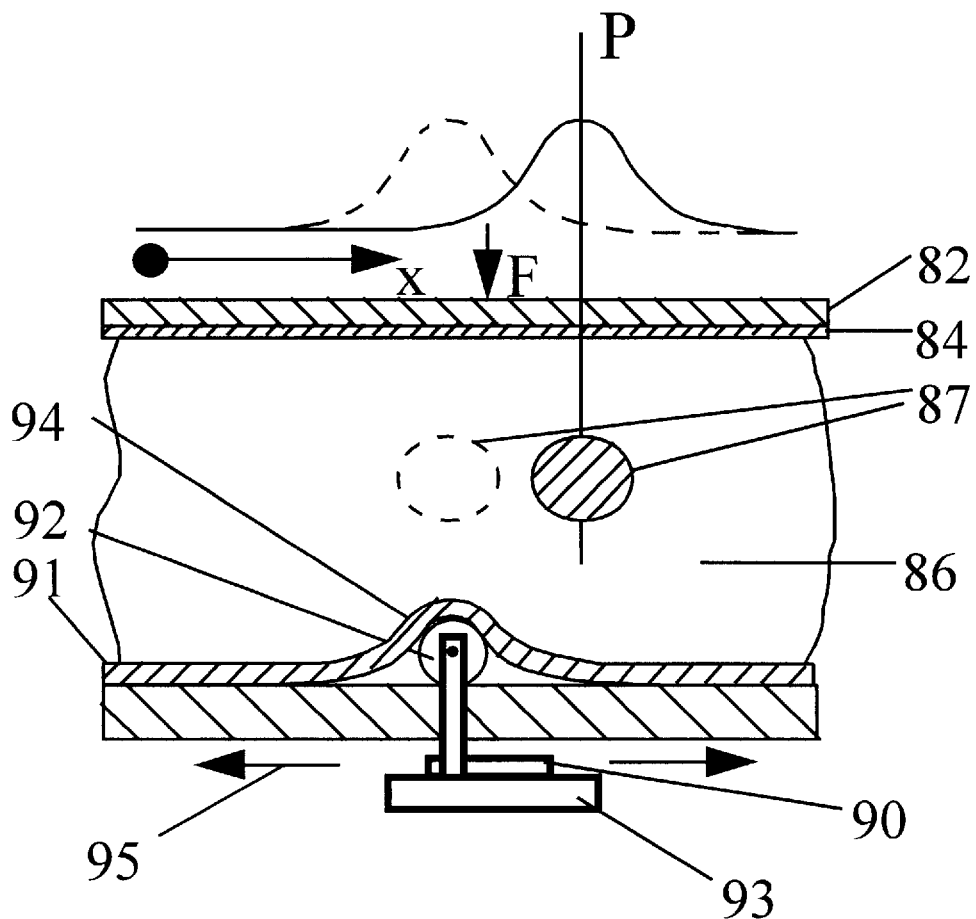
FIG. 2 illustrates a section of tissue being held against a support plate wherein a roller can be rolled along a pad directly applying deformation forces to the section of tissue.

FIGS. 1A and 1B illustrate a tumor in tissue located on the chest adjacent to ribs, and FIGS. 1B and 1C illustrate that shifting of the pressure sensor while contacting the tissue accentuates sensitivity of detection for the tumor.

In FIG. 1A, a rib cage 64 is illustrated schematically as having two ribs 66 shown in cross-section and held adjacent to each other with normal connective tissue. A quantity of tissue, such as breast tissue, is indicated at 68 and is positioned between the ribs and an outer surface of the tissue, against which a pressure plate 70 is placed, which has a pressure array 72 thereunder. Force is applied as indicated by the arrow 74 in FIG. 1A. A tumor 76 is located adjacent to and midway between the ribs 66. The distance between the centers of the ribs is indicated as (a), and the width of the ribs is indicated as (l). The height of each rib above the general support plane of the tissue is indicated by (S). The profile of pressure sensed by an array 72 is indicated at the top of FIG. 1A, with the maximum pressure detected corresponding to a position directly above the tumor 76.

In a laterally shifted position as shown in FIG. 1B, the pressure plate 70 has been shifted relative to the ribs 66. This tends to move the tumor 76 closer to one of the ribs, as shown. The tumor is now in a position where it is very near or substantially over a rib. This changed positioning of the tumor is reflected by the substantial increase in the peak of pressure profile illustrated at the top of FIG. 1B. In this case, a change in the pressure profile because of the lateral shift is represented as $\Delta P^* = P^* - P$. The lateral shift of the pressure plate 70 and pressure sensor 72 can be measured from a starting value. Although a lateral shift occurs in the X direction, the amount of shift will be indicated by "Z" in FIG. 1C. The increase of pressure sensitivity ($\Delta P^*/P$) is marked on the vertical axis, and the horizontal axis indicates an X dimension, which has a zero point at the peak pressure in FIG. 1B.

The graph of FIG. 1C calculated with the use of the mathematical approach described above illustrates the change in pressure profile ($\Delta P^*/P$)(after a lateral shift of the pressure plate 70) as a function of the distance X laterally away from the center of the pressure profile peak for $P^*(x)$. Plot 78 illustrates this relationship for a lateral shift of 7 mm of the pressure plate relative to the stationary rib cage (the difference shown between FIGS. 1A and 1B), and plot 80 corresponds to a lateral shift of 18 mm.

In this example, the distance between the center of the ribs (a) is 25 mm and (l), which is the width of the rib, is 20 mm. The other dimensional parameters are illustrated at FIG. 1C. The graphs indicate that a greater pressure measuring sensitivity is achieved in detecting a tumor in a breast (or other tissue) when the pressure plate is shifted laterally while in contact with the tissue. This is particularly true when the underlying tissue includes a bony structure such as ribs which are adjacent the tumor and over which the tumor will be moved during the shift.

In particular, the form of the invention shown in FIGS. 1A, 1B and 1C is especially useful for imaging of breast tissue with tumors situated close to the chest. When a tumor is close to a rib (see FIG. 1A) the approach described above and shown as ordinary probe techniques, such as palpating or conventional ultrasound, cannot detect the presence of the tumor. However, when the pressure sensing plate 70, having pressure sensor 72 thereon is rolled transversely to the ribs (i.e., the lateral shift) the tumor can be detected easily because of an increased resolution created by rolling the tissue. Indeed, when the tumor is moved near a rib, the rib acts much like. a piston/probe 24 thereby accentuating the peak of the pressure profile corresponding to the location of the tumor or inclusion.

The function P*(x) is shifted laterally reflecting that the peak and baseline of the pressure profile shift. This indicates that there is a harder portion of tissue between the ribs and the surface being pressed upon. If lumps are discovered in this manner, mammography or ultrasound can be utilized for analyzing the internal structures in the region of interest.

In FIG. 2, a device is shown schematically wherein a roller is moved along a section of tissue, and analysis of the differing pressure patterns is made while the roller is being so moved. As shown, a support plate 82 has a number of force sensors 84 thereon in a desired array, and the support plate 82 which also can be backed by a movable force-applying member, is acting against tissue 86. A tumor 87 is located in this tissue.

The lower support is a flexible or semi-rigid sheet 91 against which a roller 92 is pressed through the use of a support carriage 90 mounted on a suitable track 93 for lateral movement in the direction indicated by the double arrows 95. The roller 92 will thus roll along the tissue and cause a raised area 94 of the pad or support 91 to exert a greater deformation of the tissue 86 in a localized area immediately above the roller.

As it rolls along, the tumor 87 will tend to shift from the dotted line position shown at 87, and the stress relationship (as graphed in FIG. 2A) will also shift as the tumor shifts, giving an indication that there is some type of a dislocation in the tissue or different hardness tissue that will shift when the roller is rolled. Again an examination of the stress relationship can be used for determining presence of a tumor, evaluating their hardness and making judgments about its character.

Figure 3:
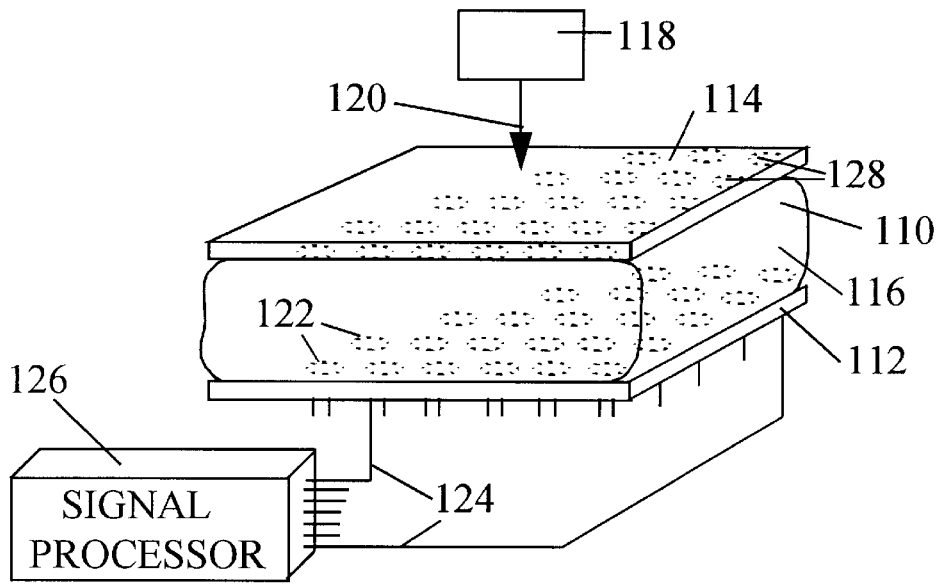
FIG. 3 is a schematic representational view of force-applying plates having an array of sensors thereon on at least one of the plates.

In FIG. 3 a simplified structure for applying deformation to living tissue wherein a quantity of tissue indicated generally at 110 is placed against a support member 112, and a pressure plate 114 is applied to an opposite side of the tissue. Tissue 110 could be breast tissue or could be muscle tissue from a forearm or upper arm, or the like. The edges of the tissue are shown as being defined by boundaries which comprise skin 116. The ends of the tissue could be joined with covering tissue such as skin or joined to other tissue, and could still connected to the human body. The section illustrated is merely intended to be illustrative of the principles involved.

A force-generating device 118 such as a load frame or compression loading frame, which is servo-controlled to provide a known amount of force indicated by the load arrow 120, will be applied to the tissue. The force generator device is capable of being relaxed as desired.

The support plate 112 has an array of individual pressure sensors 122, each of which will provide an individual signal along a line 124 to signal processing equipment 126. The equipment 126 can provide signals to suitable control systems such as in a computer or right back to the operator, so that the operator can adjust the pressure levels to achieve the desired pressure or force across the surface of the support pad 112 which altogether will provide pressure profiles obtained over the surface of the of the tissue and calculate a three-dimensional distribution of internal structures and their relative elasticities. Suitable pressure sensors indicated at 128 also can be carried on the plate 114 in order to increase resolution in detecting deeply situated tumors and evaluating their elasticity.

Thus, FIG. 3 represents a direct force application and a pressure or force readout system that gives the ability to analyze internal structure variations and calculate elasticities of these structures using the data on pressure variations across an array. The pressure sensor array can be on both sides of the tissue.

Figure 4:
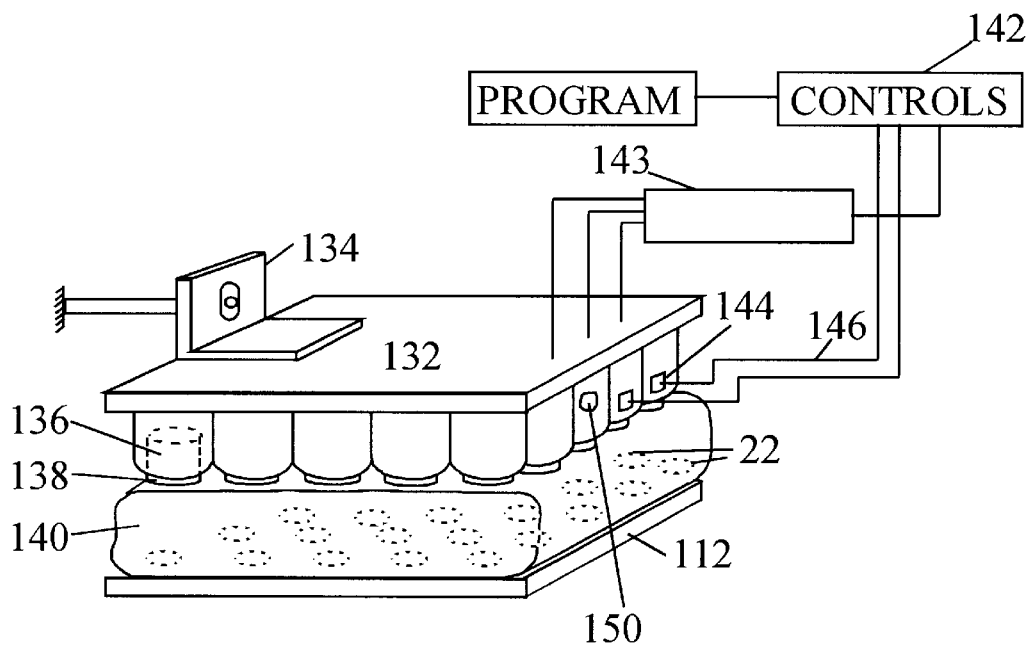
FIG. 4 is a schematic representation of a multiplicity of individual actuators compressing a portion of tissue against a reaction plate having an array of pressure or force sensors.

FIG. 4 illustrates a variation of the device of FIG. 3, and can include the same type of a backing plate 112, but in this instance the plate 114 and load member 118 are replaced by a backing plate 132 which can be adjustably fixed in spaced relation to the support plate 112, for example, by an adjustable bracket 134. The plate 132 has a number of individual fluid pressure actuators 136 mounted thereon in an array, and as shown, they are closely spaced. Each of the actuators is formed with a piston on the interior of a cylinder, and each piston has an outer rod portion 138 that has an end surface engaging tissue (indicated at 140) which is supported on the plate 112. The individual actuators 136 have controls 142 controlling suitable servovalves 143 to, in turn, control the fluid pressure in each of the actuators and thus to control the force applied in a local area by the end of the rod. A force feedback sensor indicated at 144 is provided to determine the force exerted by each actuator. Sensor 144 in turn provides a feedback signal along a line 146 to the controls 142 to indicate whether or not a pre-programmed force from a program for operation of each actuator is being met. These control systems for actuators are closed loop servosystems. Separate channels are used for each actuator and the pressure will be adjusted to equal the desired pressure. Closed loop servosystems generally use hydraulic actuators so that precise piston position, as well as the load can be obtained. The position of the rod ends 138, which form flat surfaces bearing on the tissue, can be sensed relative to the base plate 132 by using position sensors that can be internal of the actuators, that is, internally located within the cylinders, to sense the position of the respective pistons relative to the base plate 132. Such a sensor is illustrated schematically at 150 and will provide feedback signals to the controller 142 as well. The control of actuator position and/or force permits simulation of palpation by varying the force on each actuator to achieve the desired compression or displacement of underlying tissue.

Figure 5:
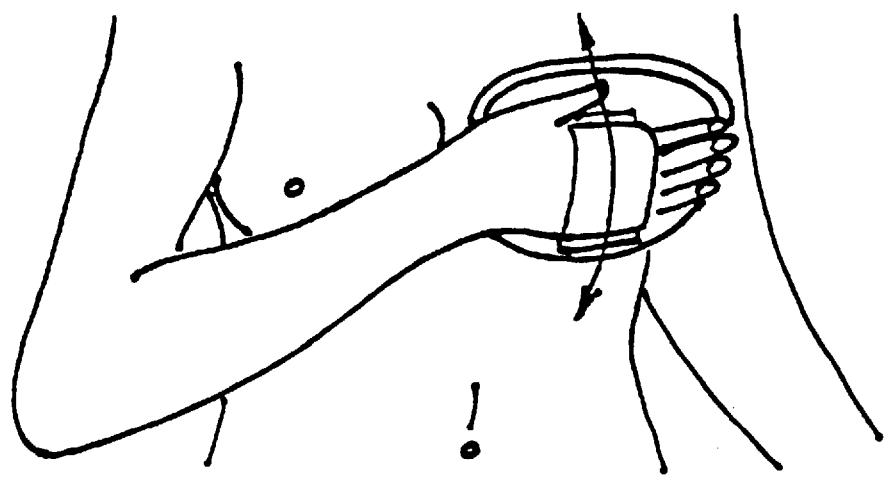
FIG. 5 is a schematic illustration of examination of a breast using a pad which incorporates a pressure sensing array in accordance with the present invention.

In an embodiment of a method and a device of the present invention shown in FIG. 5, the device is made in a form of a hand-held pad comprising a pressure sensor array and a microprocessor interfaced via a data acquisition circuit. The pad is pressed normally to the breast and is moved periodically in the direction perpendicular to the ribs as is shown in FIG. 5. Detection of a nodule is achieved by analyzing the dynamic and spatial features of the pressure pattern while the pressure sensing probe is periodically moved transversely to the ribs. A nodule within the breast that moves together with the surrounding tissue over the ribs produces additional periodic stress on the pressure sensing elements situated on the flat surface contacting the breast. The principle 6f detection of nodules is illustrated in FIGS. 1A, 1B, and 1C. The graph of FIG. 11C illustrates the change in pressure profile after a particular lateral shift of a probe. The graph clearly shows how significant the increase of the contribution of the tumor is in the pressure profile after a lateral shift (20% in this particular case). The ribs play a role as an amplifier of the "signal" from the tumor. Periodic movement of the probe across the ribs plus spatial periodicity of the ribs provide unique possibilities for filtering out the "signals" from targets other than lesions which are to be detected. This device will be able to detect objectively the presence of lumps in a breast and provide a warning signal. The result of examination is displayed in the form of a sound or light signal.

Figure 6A:
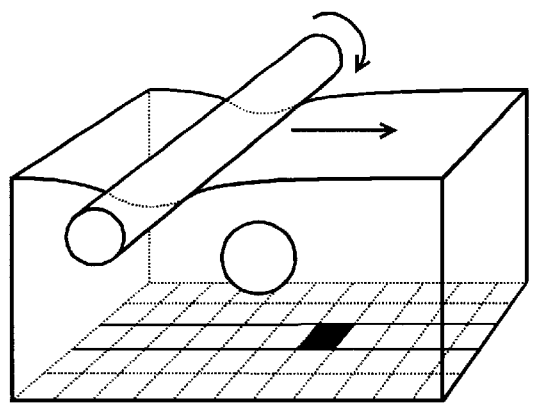
FIG. 6A is a perspective illustration of an experiment done with the use of a rubber model of a tissue with an inclusion therein.
Figure 6B:
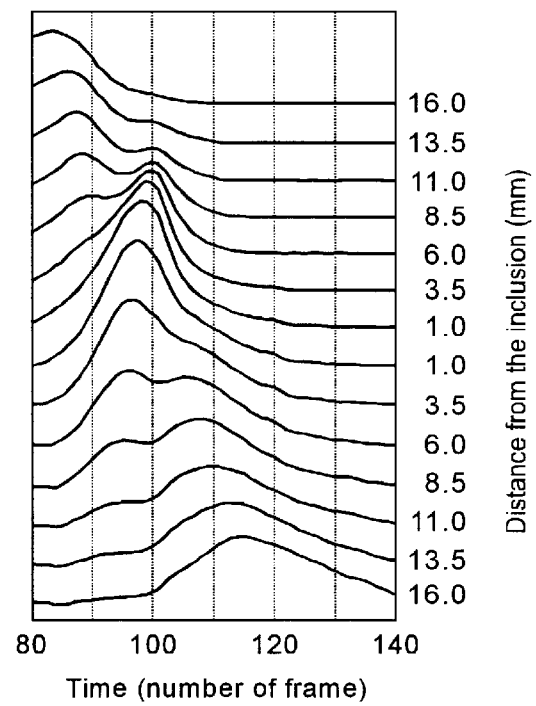
FIG. 6B is a plot of the pressure profiles obtained from the sensors situated at different distances from the inclusion using the experimental model shown in FIG. 6B.
Figure 6C:
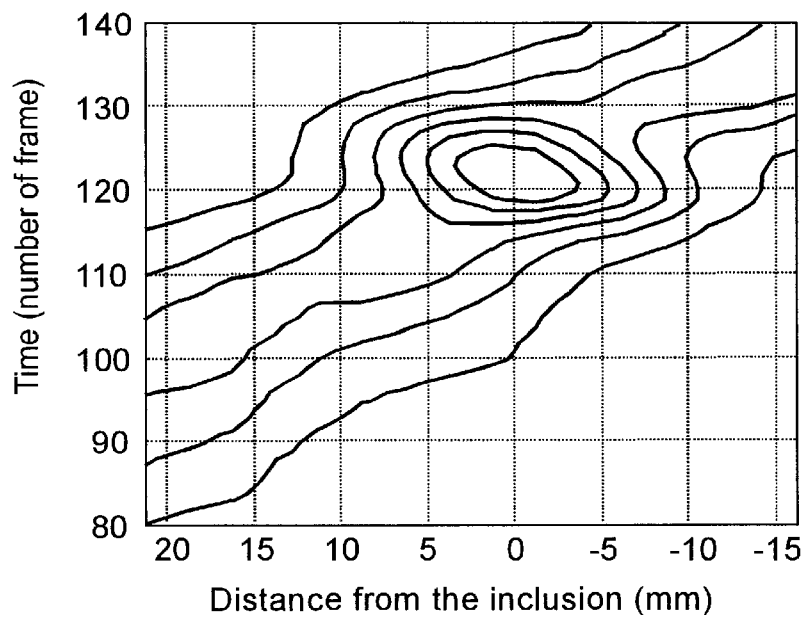
FIG. 6C is a topographic representation of the data shown in FIG. 6A.

FIGS. 6A, 6B, and 6C describe a model experiment illustrating the principle of detection of a nodule in the case when there is a relative motion of a linear support member (simulating a rib), in respect to the nodule and the pressure sensing array. FIG. 6A shows a rubber model 210 with dimensions 50×40×25 mm having in its center a hard inclusion 230 with diameter placed on a commercially available pressure sensor array 215 Tekscan I-SCAN 100 manufactured by Tekscan Inc., Boston, Mass. The array 215 consists of conductive rows and columns whose intersecting points form sensing locations. The rows and columns are separated by a material which varies its electrical resistance with applied force, and thus each intersection becomes a force sensor. Sensors are schematically shown in FIG. 6A as squares at the lower surface of the model. A roller 294 made of a metal rod having a diameter of 15 mm was rolled over the model 210 and signals from the sensors along the row beneath the inclusion 230 (as shown in the FIG. 6A) were recorded in time. FIG. 6B shows pressure temporal profiles for the sensors situated at a different distance from the inclusion (the distance for each profile is given at the left side of the figure). One can clearly see how the profiles differ depending on the relative position of the sensor and the inclusion. A number of temporal and spatial features of the signal can be used to design an algorithm for detecting the presence of a nodule: the amplitude of the signal, the width of the peak, the shape of the pressure profile, etc. FIG. 6C shows the data of FIG. 6B as a topographic map with the clear image of the inclusion 230.

Figure 7:
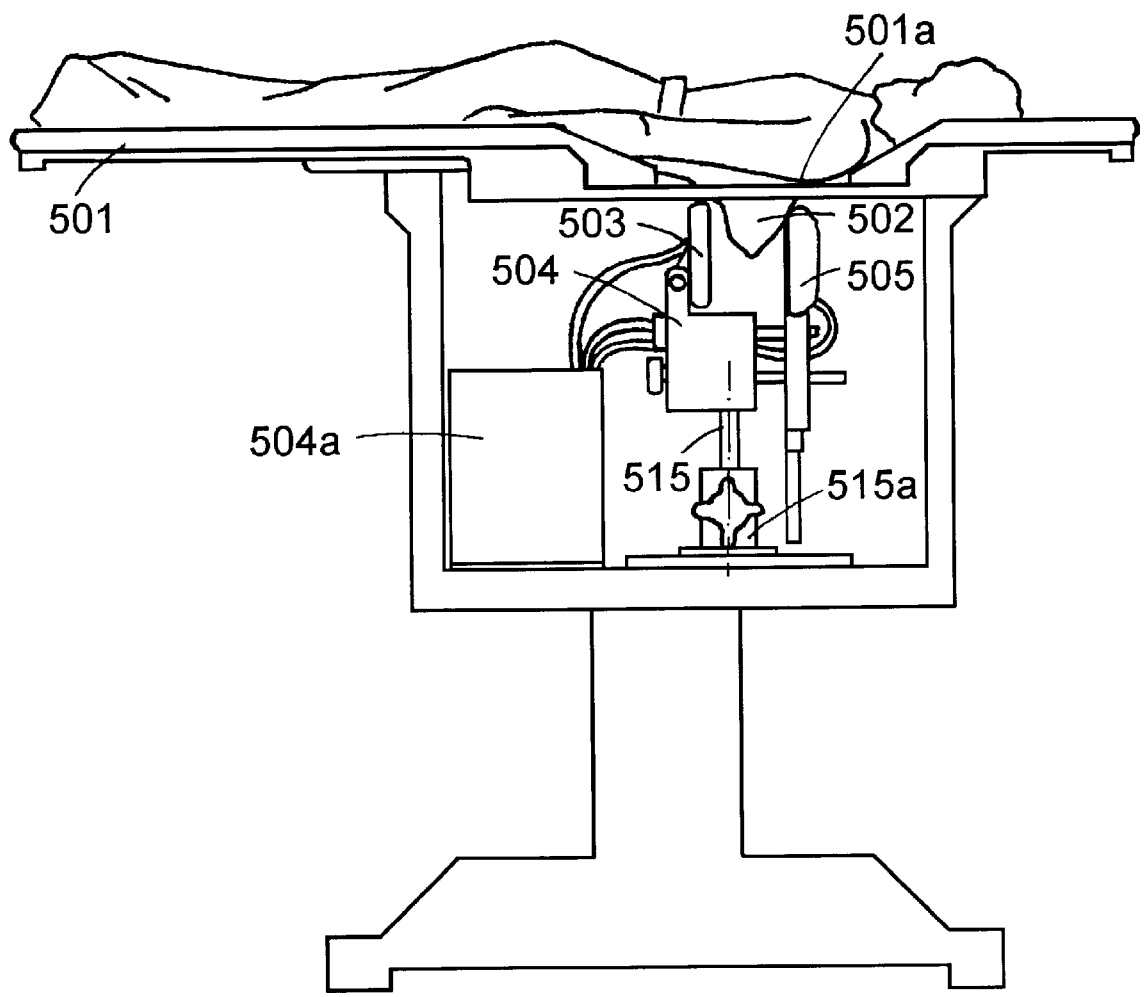
FIG. 7 is a front elevational view of clinical apparatus for performing mechanical imaging of a breast in accordance with the present invention.

Another embodiment of the invention shown in FIGS. 7–11 is a clinical device for imaging the mechanical structure of the examined breast and diagnosing diseases accompanied by changes in the elasticity of breast tissue. The overall view of the device for mechanical imaging of the breast is shown in FIG. 7. The patient lays face down on the table 501 so that the examined breast 502 is located and loosely inserted into the breast aperture 501a. Such an examination position allows the pectoral muscles to relax and the chest to expand into the breast aperture for greater access to the breast tissue adjacent to the chest wall. Inside the breast aperture, the breast is placed between the holder 505 of the mechanical scanning unit and the pressure sensor array 503, and consequently compressed. Both the support 504 of the pressure sensor array and the holder 505 of the scanning unit can rotate along the vertical axis with a revolving holder 515 in its positioning base 515a.

The signals from the pressure sensing elements of the pressure sensor array are buffered and multiplexed directly near the pressure sensor array. The lines conducting these multiplexed signals along with additional pressure signals, and positioning control signals are brought to the electronics compartment 504a where part of the microcomputer interface, pressure signal decoding, and motor driving circuitry is located. The entire system is controlled by an external CPU from a personal computer.

Figure 8:
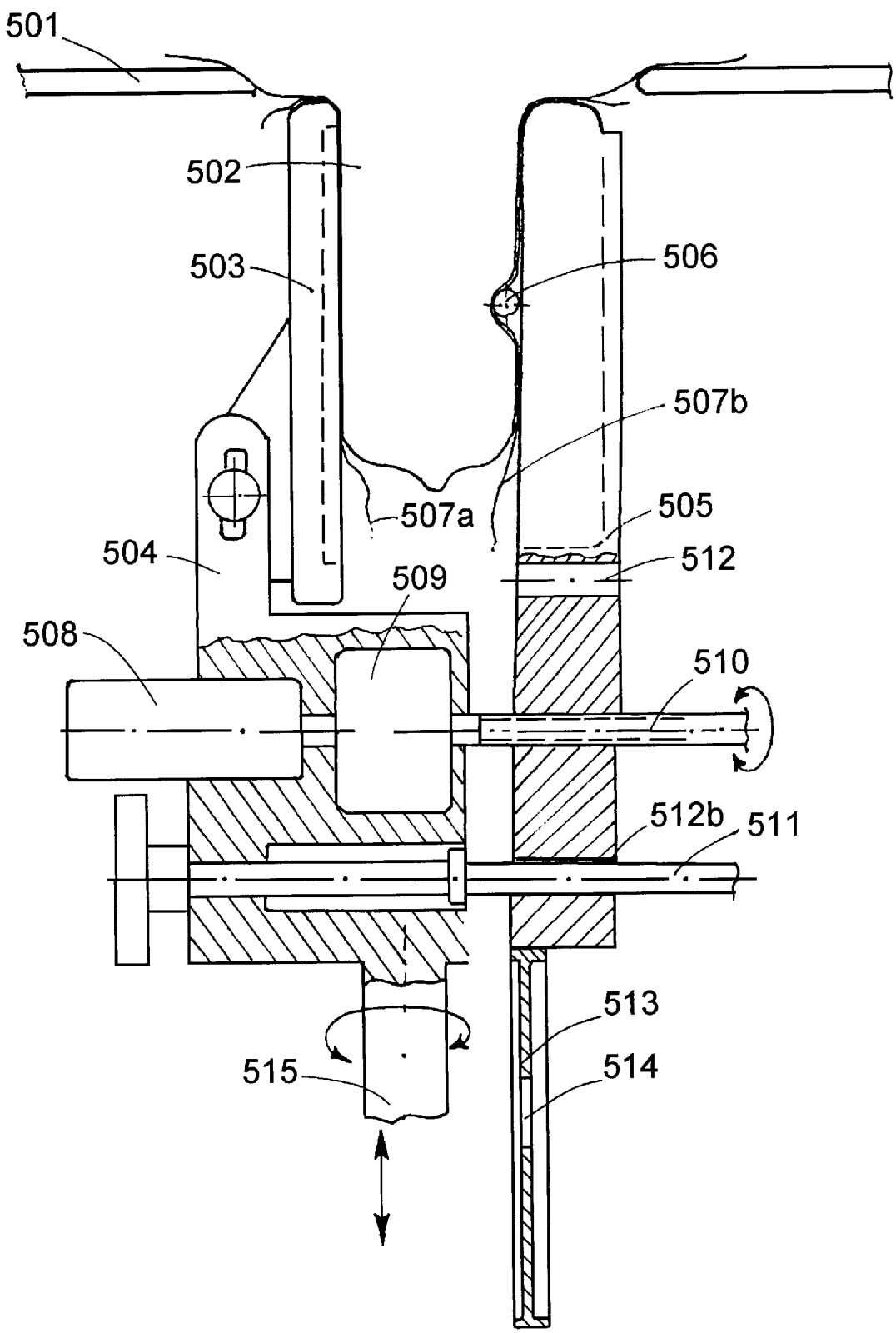
FIG. 8 is a sectional view of an embodiment of the mechanical scanning unit of the device shown in FIG. 7 and which employs a roller.

FIG. 8 shows the compression mechanism and positioning of the scanning unit and the pressure sensor. The motor 508 controls the level of breast compression through the reduction gear 509 and retractable screw rod 510. Pressure sensor array 503 is mounted on the support 504 which can rotate to the desired position with respect to the examined breast with the revolving holder 515. The holder 505 comprises transparent exchangeable plate 513 with biopsy window 514. When the scanning unit holder 505 is rotated by 180° around the screw rod 510 and fixed in the position by the fixing pin 511 in a fixing pin hole 512a, the exchangeable plate 513 is in the place of contact with the breast. The exchangeable plate contains a biopsy window 514 which may be situated in different parts of the exchangeable plate 513 to provide access to the target lesion in the breast to be reached by the aspiration needle or biopsy gun. Disposable polymer films 507a and b are replaced after each examination. The surface of the film 507b facing the dynamic pressure element (roller in this case) 506 is covered with a lubricant to decrease the friction while moving the pressure element over the breast. In a version of this embodiment, the pressure element is a roller moving in the vertical direction (FIGS. 8, 9A and 9B). In another version, the pressure element is an indenter moving in all the three dimensions (FIGS. 10A and 10B, 11A–C).

FIGS. 9A and 9B show the mechanical scanning and measuring unit incorporating a roller in more detail. The base plate 524 is used to produce a controlled pressure on the examined breast. The moving roller 506 acts as the additional dynamic pressure element. The roller 506 is supported by two bearings, 516a and b, which can move vertically along the base plate 524 in the two guide slots, 517a and 517b respectively. The movement of the bearings is controlled by the rotation of the motor 523. The torque of the motor is transferred through gear wheels 521 and 522 to the axis 520. The axis 520 is firmly attached to the pulleys 519b and 519d and through the cables 518a and 518b to the rolling pulleys 519a and 519c, and thus moving the bearings 516a and 516b, and the roller 506, in the vertical direction.

The use of a roller to increase sensitivity of the pressure sensing array to the presence of a tumor in the tissue was discussed for FIGS. 2, and 6A, 6B, and 6C.

Figures 10A, 10B:
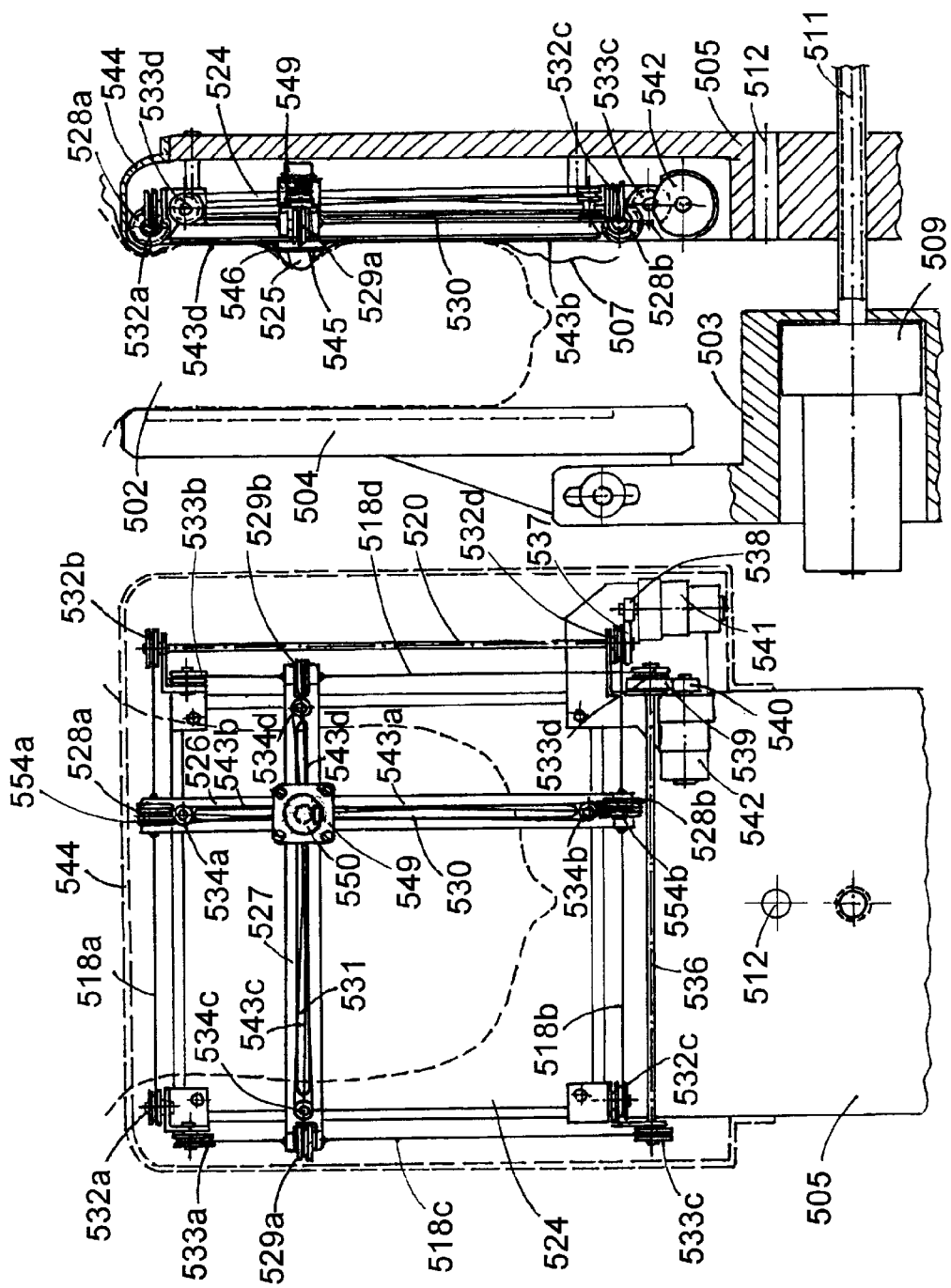
FIG. 10A is a front view of the indenter motion control system of the mechanical scanning unit.
FIG. 10B is a detailed sectional side view of the indenter motion control system of the mechanical scanning unit, as in FIG. 10A.

FIGS. 10A and 10B show the construction of the mechanical scanning and measuring unit with the movable and extendible indenter 525 which produces a local mechanical stress in the breast. The indenter is attached to two mutually perpendicular cables 543a and b. The cables pass through the pulleys 528a and b, and 529a and b. The pulleys are mounted at the ends of movable guide bars. The guide bars 526 and 527 are attached respectively to the cables 518a, b, and 518c and d, passing through the pulleys 532a, b, c, and d, and 533a, b, c, and d. The cables are pulled by rotating axes 535 and 536, driven by motors 541 and 542 through respective gear wheels 537, 538, and 539, 540.

FIGS. 11A, 11B, and 11C show the indenter movement mechanism in more detail. The coordinating element 525a which has a disk-shaped base is placed in the slots 530 and 531 respectively of the guide bars 526 and 527 (see FIGS. 10A and 10B). The base of the coordinating element 525a is connected to the cables 543a and b on the side of the base plate 524 opposite to the breast. The cables 543a and 543b are connected to the base of the coordinating element 525a by the opposite ends. The cable 543a passes through the main pulleys 528a and b and through the auxiliary pulleys 534a and b. Similarly, the cable 534b passes through the main pulleys 529a and b and auxiliary pulleys 534c and d. The base of the indenter is firmly attached to the intersection of the cables 543a and 543b on the side of the base plate 524 facing the breast in such a way that the indenter always tracks the position of the coordinating element 525a defined by the position of the guide bars 526 and 527.

An important feature of this embodiment is that a film pressure sensor 545 is attached to the base of the indenter at the surface facing the base plate. The cables 543a and b are made of metal strings and serve also as electrical connectors for the pressure sensor. The electrical connection of these cables with the measuring circuit is provided by spring contacts (not shown in figures). The sensor measures the force the indenter applies to the breast. This is similar to having the second pressure sensing array on the side opposite to the array 503. Dependence of the pressure on the position of the indenter over the scanned area of the breast provides a virtual stress pattern over the breast surface facing the indenter. In addition to the 2D motion of the indenter along the surface of the base plate 524, it can also be extended normally to the breast, thus providing a possibility to fully mimic various motions of a palpating finger.

The extension of the indenter is illustrated in FIGS. 11A, 11B, and 11C. The indenter is moved by a lead screw 546 and thread bushing 547 pulled by a cable 552. The cable passes through the pulleys 550a and 550b mounted on the movable guide bar 526 and is pulled by a spool fixed on the axis of the motors 552.

Protective housing 544 prevents the examined breast from a direct contact with the moving pulleys and cables.

In the embodiment shown in FIGS. 10–11, motion of the indenter over the breast results in complex temporal and spatial variations of the pressure sensors signals from both sides of the breast. The ability of the indenter to "sense" the tissue by extending towards the breast, or making a combined motion in both normal and tangential directions, like an examining human finger does, provides a new dimension in the further processing of the data. In addition, the use of an extendible indenter provides a possibility to create highly localized stress which facilitates the detection of nodules.

The motion of the indenter can be controlled either automatically by a computer using a special program designed for optimal scanning, or manually. Manual control can be done in an interactive mode, when an operator observing the stress patterns on the screen of the computer moves the indenter over a region of interest in the breast using a joystick or a mouse. The mouse provides a possibility to control the motion both tangentially, along the breast surface, and normally, towards the breast. The normal motion control button of the mouse can be equipped by a force sensors, so that an operator has a feeling of changes in the local stress caused by the indenter. Consequently, he/she can establish a closer feedback control over the scanning procedure by directly observing the changes in the stress pattern on the screen of the computer resulting from the pressing the normal motion control button with a given force.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method of identifying a region within a tissue portion of a human breast having a different elasticity than the surrounding tissue, said method comprising the steps of:
   causing a deformation of an examined tissue portion of said breast;
   detecting temporal and spatial changes in a pressure pattern caused by said deformation measured simultaneously at a plurality of locations on an accessible surface of the tissue portion;
   defining a model of the tissue portion with homogenous tissue and with boundary conditions corresponding to the examined tissue portion;
   evaluating respective temporal and spatial changes in the pressure pattern for said defined model under the same loading conditions as in the detecting step;
   adjusting iteratively said defined model by varying a spatial distribution of modulus of elasticity in the model to minimize the difference between temporal and spatial changes in the pressure pattern obtained in the detecting step and the respective temporal and spatial changes in the pressure pattern evaluated for the adjusted model, thereby obtaining spatial distribution of elasticity modulus in the tissue portion; and
   visualizing and displaying spatial distribution of modulus of elasticity in said adjusted model of the examined tissue portion for indicating the presence and location of a differing elasticity region of tissue within the tissue portion.

2. The method of claim 1 wherein the causing a deformation step further comprises creating strain and stress in the tissue portion placed between a pressure sensing array and a support member by moving the pressure sensing array and the support member in respect to each other.

3. The method of claim 2 wherein the causing a deformation step further comprises urging the tissue of the tissue portion toward the support member.

4. The method of claim 2 wherein the causing a deformation step further comprises shifting laterally the surface of the tissue portion along the support member, thereby causing shear deformation in the tissue portion.

5. The method of claim 2, wherein said support member is a rib cage.

6. The method of claim 5 wherein the causing a deformation step further comprises shifting laterally the tissue portion along the rib cage in direction perpendicular to the ribs.

7. A device of identifying a region with a tissue portion of human breast having a different elasticity than the surrounding tissue, said method comprising the steps of:
   means for causing a deformation of an examined tissue portion of said breast, thereby causing stress and strain in the examined tissue portion;
   means for detecting temporal and spatial changes in a pressure patter measured on the surface of the examined tissue portion;
   means for defining a model of the tissue portion with homogenous tissue and with boundary conditions corresponding to the examined tissue portion;
   means for evaluating respective temporal and spatial changes in the pressure pattern for said defined model under the same loading conditions as in the detecting step;

means for comparing the temporal and spatial changes in the pressure pattern obtained in the detecting step and the temporal and spatial changes in the pressure pattern evaluated in the evaluating step, the difference indicating the presence and location of a differing elasticity region of tissue within the tissue portion;

means for adjusting iteratively said defined model by varying a spatial distribution of modulus of elasticity in the model to minimize the difference between temporal and spatial changes in the pressure pattern obtained in the detecting step and the respective temporal and spatial changes in the pressure pattern evaluated for the adjusted model, thereby obtaining spatial distribution of elasticity modulus in the tissue portion;

means for visualizing and displaying spatial distribution of modulus of elasticity in said adjusted model of the examined tissue portion for indicating the presence and location of a differing elasticity region of tissue within the tissue portion; and wherein said device is a hand-held unit comprising a pressure sensing array connected to a microprocessor capable of detecting regions of the tissue within a tissue portion having a different elasticity than the surrounding tissue and producing a warning signal.

8. A device of identifying a region within a tissue portion of a human breast having a different elasticity than the surrounding tissue, said method comprising the steps of:

means for causing a deformation of an examined tissue portion of said breast, thereby causing stress and strain in the examined tissue portion;

means for detecting temporal and spatial changes in a pressure pattern measured on the surface of the examined tissue portion;

means for defining a model of the tissue portion with homogenous tissue and with boundary conditions corresponding to the examined tissue portion;

means for evaluating respective temporal and spatial changes in the pressure pattern for said defined model under the same loading conditions as in the detecting step;

means for comparing the temporal and spatial changes in the pressure pattern obtained in the detecting step and the temporal and spatial changes in the pressure pattern evaluated in the evaluating step, the difference indicating the presence and location of a differing elasticity region of tissue within the tissue portion;

means for adjusting iteratively said defined model by varying a spatial distribution of modulus of elasticity in the model to minimize the difference between temporal and spatial changes in the pressure pattern obtained in the detecting step and the respective temporal and spatial changes in the pressure pattern evaluated for the adjusted model, thereby obtaining spatial distribution of elasticity modulus in the tissue portion;

means for visualizing and displaying spatial distribution of modulus of elasticity in said adjusted model of the examined tissue portion for indicating the presence and location of a differing elasticity region of tissue within the tissue portion; and wherein the means for causing a deformation of the tissue portion comprises an additional means producing local deformation of the surface of the tissue portion, the second deformation occurring over a substantially smaller area than the region of the first deformation, the local deformation producing means is a roller moveable along the surface of the breast.

9. A device of identifying a region within a tissue portion of a human breast having a different elasticity than the surrounding tissue, said method comprising the steps of:

means for causing a deformation of an examined tissue portion of said breast, thereby causing stress and strain in the examined tissue portion;

means for detecting temporal and spatial changes in a pressure pattern measured on the surface of the examined tissue portion;

means for defining a model of the tissue portion with homogenous tissue and with boundary conditions corresponding to the examined tissue portion;

means for evaluating respective temporal and spatial changes in the pressure pattern for said defined model under the same loading conditions as in the detecting step;

means for comparing the temporal and spatial changes in the pressure pattern obtained in the detecting step and the temporal and spatial changes in the pressure pattern evaluated in the evaluating step, the difference indicating the presence and location of a differing elasticity region of tissue within the tissue portion;

means for adjusting iteratively said defined model by varying a spatial distribution of modulus of elasticity in the model to minimize the difference between temporal and spatial changes in the pressure pattern obtained in the detecting step and the respective temporal and spatial changes in the pressure pattern evaluated for the adjusted model, thereby obtaining spatial distribution of elasticity modulus in the tissue portion;

means for visualizing and displaying spatial distribution of modulus of elasticity in said adjusted model of the examined tissue portion for indicating the presence and location of a differing elasticity region of tissue within the tissue portion; and wherein the means for causing a deformation of the tissue portion comprises an additional means producing local deformation of the surface of the tissue portion, the second deformation occurring over a substantially smaller area than the region of the first deformation, the local deformation producing means is an extendible indenter, capable of moving in all three dimensions.

10. The device of claim 9 further comprising:

a pressure sensor measuring the pressure exerted by the indenter to the tissue;

a mouse controlling the position of the indenter by moving the mouse over a pad and controlling the pressure exerted by the indenter on the tissue using a button controlled by an operator's finger, so that the operator has a feeling of changes in the local stress caused by the indenter;

computer means for analyzing temporal and spatial changes in pressure exerted by the indenter on the tissue portion and for evaluating the presence, location and dimentions of regions of the tissue within the investigated tissue portion having a different elasticity than the surrounding tissue;

a means for displaying an image of the tissue portion with the region of a different elasticity to provide a feedback information to an operator about the relative position of the probing indenter and the applied pressure.

* * * * *